(12) United States Patent
Daines et al.

(10) Patent No.: US 6,608,059 B1
(45) Date of Patent: Aug. 19, 2003

(54) FATTY ACID SYNTHASE INHIBITORS

(75) Inventors: Robert A. Daines, King of Prussia, PA (US); Israil Pendrak, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/296,774

(22) PCT Filed: Jun. 27, 2001

(86) PCT No.: PCT/US01/20458

§ 371 (c)(1),
(2), (4) Date: Dec. 13, 2002

(87) PCT Pub. No.: WO02/00646

PCT Pub. Date: Jan. 3, 2002

Related U.S. Application Data

(60) Provisional application No. 60/214,280, filed on Jun. 29, 2000.

(51) Int. Cl.$^7$ ............... C07D 403/06; C07D 413/14; A61K 31/404

(52) U.S. Cl. ............... 514/235.2; 514/364; 514/374; 514/381; 544/132; 544/144; 548/138; 548/235; 548/250; 548/252; 548/253

(58) Field of Search ............... 544/132, 144; 548/138, 250, 235, 252, 253; 514/235.2, 364, 374, 381

(56) References Cited

U.S. PATENT DOCUMENTS

| | | | |
|---|---|---|---|
| 5,684,034 A | 11/1997 | Bach et al. | 514/419 |
| 5,708,016 A | 1/1998 | Fauchere et al. | 514/381 |
| 6,486,211 B1 * | 11/2002 | Daines et al. | 514/714 |

* cited by examiner

*Primary Examiner*—Deepak Rao
(74) *Attorney, Agent, or Firm*—Soma G. Simon; Mary E. McCarthy; Charles M. Kinzig

(57) ABSTRACT

This invention relates to the use of compounds as inhibitors of the fatty acid synthase FabH.

4 Claims, No Drawings

FATTY ACID SYNTHASE INHIBITORS

This application is a 371 of PCT/US 01/20458 filed Jun. 27, 2001 which claims the benefit of U.S. Provisional Application 60/214,280 filed Jun. 29, 2000.

FIELD OF THE INVENTION

This invention relates to the use of compounds as inhibitors of the fatty acid synthase FabH.

BACKGROUND OF THE INVENTION

The pathway for the biosynthesis of saturated fatty acids is very similar in prokaryotes and eukaryotes. However, although the chemical reactions may not vary, the organization of the biosynthetic apparatus is very different. Vertebrates and yeasts possess type I fatty acid synthases (FASs) in which all of the enzymatic activities are encoded on one or two polypeptide chains, respectively. The acyl carrier protein (ACP) is an integral part of the complex. In contrast, in most bacterial and plant FASs (type II) each of the reactions are catalyzed by distinct monofunctional enzymes and the ACP is a discrete protein. Mycobacteria are unique in that they possess both type I and II FASs; the former is involved in basic fatty acid biosynthesis whereas the latter is involved in synthesis of complex cell envelope lipids such as mycolic acids. There therefore appears to be considerable potential for selective inhibition of the bacterial systems by broad-spectrum antibacterial agents (Jackowski, S. 1992. In Emerging Targets in Antibacterial and Antifungal Chemotherapy. Ed. J. Sutcliffe & N. Georgopapadakou. Chapman & Hall, New York; Jackowski, S. et al. (1989). J. Biol. Chem. 264, 7624–7629.)

The first step in the biosynthetic cycle is the condensation of malonyl-ACP with acetyl-CoA by FabH. In subsequent rounds malonyl-ACP is condensed with the growing-chain acyl-ACP (FabB and FabF, synthases I and II respectively). The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (FabI). Further rounds of this cycle, adding two carbon atoms per cycle, eventually lead to palmitoyl-ACP whereupon the cycle is stopped largely due to feedback inhibition of FabH and I by palmitoyl-ACP (Heath, et al, (1996), J.Biol.Chem. 271, 1833–1836). FabH is therefore a major biosynthetic enzyme which is also a key regulatory point in the overall synthetic pathway (Heath, R. J. and Rock, C. O. 1996. J.Biol.Chem. 271, 1833–1836; Heath, R. J. and Rock, C. O. 1996. J.Biol.Chem. 271, 10996–11000).

The antibiotic thiolactomycin has broad-spectrum antibacterial activity both in vivo and in vitro and has been shown to specifically inhibit all three condensing enzymes. It is non-toxic and does not inhibit mammalian FASs (Hayashi, T. et al., 1984. J. Antibiotics 37, 1456–1461; Miyakawa, S. et al., 1982. J. Antibiotics 35, 411–419; Nawata, Y et al., 1989. Acta Cryst. C45, 978–979; Noto, T. et al., 1982. J. Antibiotics 35, 401–410; Oishi, H. et al., 1982. J. Antibiotics 35, 391–396. Similarly, cerulenin is a potent inhibitor of FabB & F and is bactericidal but is toxic to eukaryotes because it competes for the fatty-acyl binding site common to both FAS types (D'Agnolo, G. et al.,1973. Biochim. Biophys. Acta. 326, 155–166). Extensive work with these inhibitors has proved that these enzymes are essential for viability. Little work has been carried out in Gram-positive bacteria.

There is an unmet need for developing new classes of antibiotic compounds that are not subject to existing resistance mechanisms. No marketed antibiotics are targeted against fatty acid biosynthesis, therefore it is unlikely that novel antibiotics of this type would be rendered inactive by known antibiotic resistance mechanisms. Moreover, this is a potentially broad-spectrum target. Therefore, FabH inhibitors would serve to meet this unmet need.

SUMMARY OF THE INVENTION

This invention comprises indole derivatives and pharmaceutical compositions containing these compounds and their use as FabH inhibitors that are useful as antibiotics for the treatment of Gram positive and Gram negative bacterial infections.

This invention further constitutes a method for treatment of a Gram negative or Gram positive bacterial infection in an animal, including humans, which comprises administering to an animal in need thereof, an effective amount of a compound of this invention.

DETAILED DESCRIPTION OF THE INVENTION

The compounds of this invention are represented by Formula (I):

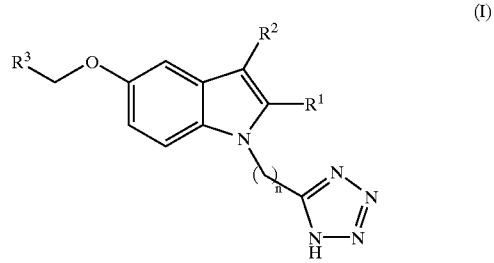

wherein, $R^1$ is selected from the group consisting of H, $CO_2R^4$, $COR^4$, $CONR^5R^6$, $CH(OH)R^4$, $CR^4$=$NOR^4$, heteroaryl and substituted heteroaryl;

$R^2$ is selected from the group consisting of H, $COR^4$, and $CH(OH)R^4$;

$R^3$ is selected from the group consisting of aryl, substituted aryl, heteroaryl and substituted heteroaryl;

$R^4$ is H or lower alkyl;

$R^5$ and $R^6$ are, independently, H, or lower alkyl or, together, form a 5 or 6 membered ring selected from the group consisting of piperidine, piperazine, pyrrolidine, morpholine and hydroxy piperidine; and n is an integer from 1 to 6.

Also included in the invention are pharmaceutically acceptable salt complexes.

Preferred substituted heteroaryl moieties include oxadiazole and oxazole.

As used herein, "alkyl" means both straight and branched chains of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like. The alkyl may carry substituents such as hydroxy, carboxy, alkoxy, and the like.

The term "cycloalkyl" is used herein to mean cyclic rings, preferably of 3 to 8 carbons, including but not limited to cyclopropyl, cyclopentyl, cyclohexyl, and the like.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

As used herein, "aryl" means phenyl and naphthyl and substituted aryl such as hydroxy, carboxy, halo, alkoxy, methylenedioxy, and the like.

As used herein, "heteroaryl" means a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, and benzimidazole.

As used herein, preferred aryl substituents include halo, including chloro, fluoro, bromo and iodo, in any combination; $C_{1-10}$ alkyl, $C_{1-10}$ alkoxy, aryloxy, or heteroaryloxy.

The compounds of this invention may contain one or more asymmetric carbon atoms and may exist in racemic and optically active forms. All of these compounds and diastereomers are contemplated to be within the scope of the present invention.

Some of the compounds of this invention may be crystallised or recrystallised from solvents such as organic solvents. In such cases solvates may be formed. This invention includes within its scope stoichiometric solvates including hydrates as well as compounds containing variable amounts of water that may be produced by processes such as lyophilisation.

Since the antibiotic compounds of the invention are intended for use in pharmaceutical compositions it will readily be understood that they are each provided in substantially pure form, for example at least 60% pure, more suitably at least 75% pure and preferably at least 85%, especially at least 95% pure, particularly at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 49% of a compound of the formula (I) or salt thereof.

Preferred compounds of the present invention include:

5-(2,6-dichlorobenzyloxy)-1-[3-(1H-tetrazol-5-yl)propyl]-1H-indole-2-carboxylic acid ethyl ester;

1-{5-(2,6-dichlorobenzyloxy)-1-[3-(1H-tetrazol-5-yl)propyl]-1H-indol-2-yl}-1-morpholin-4-yl-methanone;

5-(2,6-dichlorobenzyloxy)-1-[3-(1H-tetrazol-5-yl)propyl]-1H-indole-2-carboxylic acid isobutyl amide;

5-(2,6-dichlorobenzyloxy)-1-[3-(1H-tetrazol-5-yl)propyl]-1H-indole-2-carboxylic acid diethylamide;

5-(2,6-dichlorobenzyloxy)-3-formyl-1-[3-(1H-tetrazol-5-yl)propyl]-1H-indole-2-carboxylic acid ethyl ester;

5-(2,6-dichlorobenzyloxy)-2-(3-methyl-[1,2,4]oxadiazol-5-yl)-1-[3-(1H-tetrazol-5-yl)propyl]-1H-indole;

5-(2,6-dichlorobenzyloxy)-1-[3-(1H-tetrazol-5-yl)propyl]-1H-indole;

1-{5-(2,6-dichlorobenzyloxy)-1-[3-(1H-tetrazol-5-yl)-propyl]-1H-indol-3-yl}propan-1-one;

5-(2,6-dichlorobenzyloxy)-1-[3-(1H-tetrazol-5-yl)propyl]-1H-indole-2-carbaldehyde-O-methyl oxime; and 5-(2,6-dichlorobenzyloxy)-2-(oxazol-5-yl)-1-[3-(1H-tetrazol-5-yl)propyl]-1H-indole.

Methods of Preparation

Compounds of formula (I) wherein $R^1$ is an ethyl ester, $R^2$ is H, $R^3$ is 2,6-dichlorophenyl and n=3 were prepared by the method described in Scheme 1.

Scheme 1

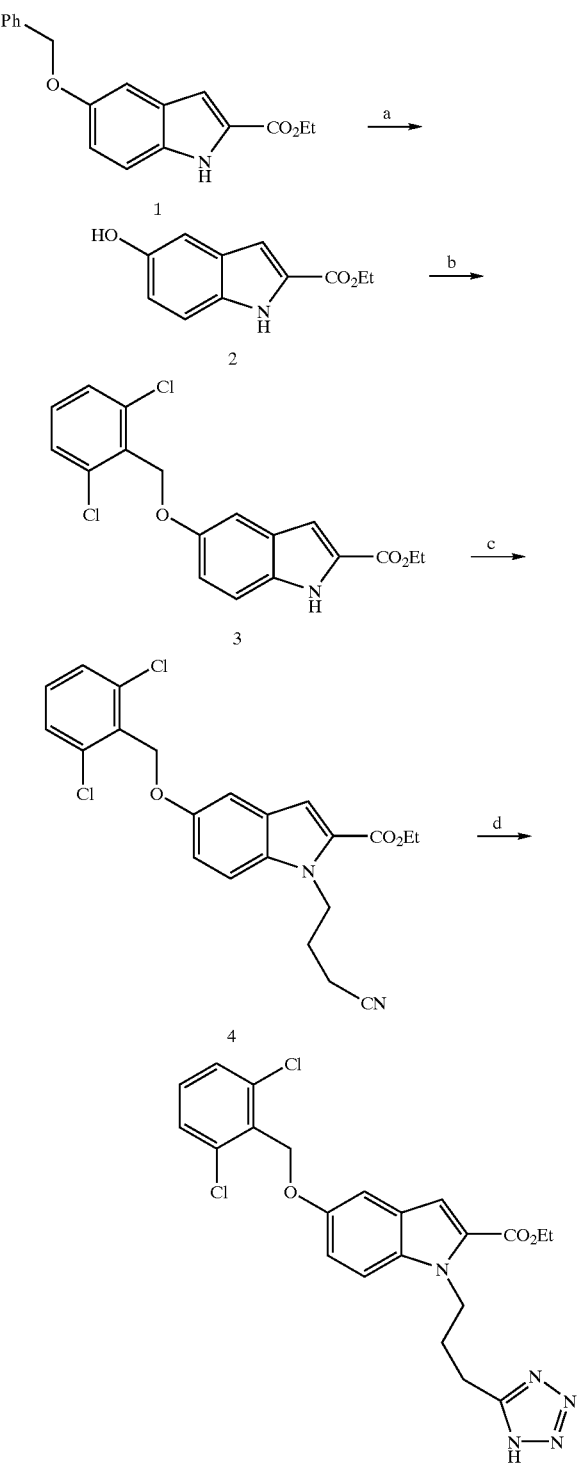

a) 10% Pd/C, $H_2$, EtOH; b) 2,6-dichlorobenzyl chloride, $Cs_2CO_3$, DMF; c) NaH, 4-bromobutyronitrile, DMF; d) $Me_3Si-N_3$, $Bu_2Sn=O$, toluene, reflux Indole ethyl ester 1, Scheme 1, (Aldrich) was debenzylated via catalytic hydrogenation to provide the 5-hydroxy indole 2. The 5-hydroxyl was then alkylated using the desired halide-containing reagent, in this example 2,6-dichlorobenzyl chloride, using a suitable base such as cesium or potassium carbonate, providing indole 3. The indole nitrogen was next alkylated with 4-bromobutyronitrile, using NaH as a base, to provide the tetrazole precursor 4. The nitrile moiety of 4 was next converted to the tetrazole via reaction with azide according to published methods. In this particular example, the method using azidotrimethylsilane and dibutyltin oxide in refluxing toluene was chosen. Thus tetrazole 5 was obtained.

Compounds of formula (I) wherein $R^1$ is an amide, morpholino amide for this example, $R^2$ is H, $R^3$ is 2,6-dichlorophenyl and n=C3 were prepared by the method described in Scheme 2.

Scheme 2

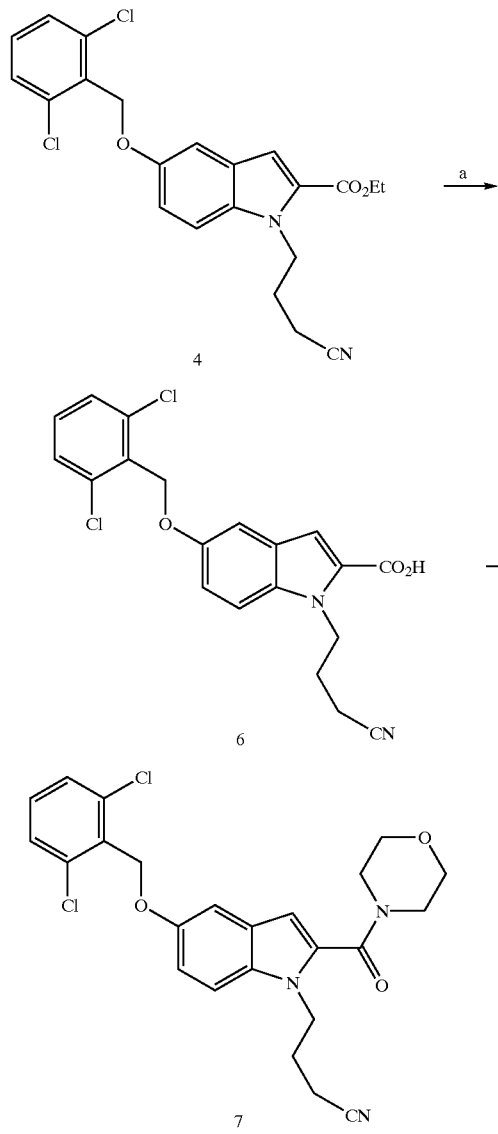

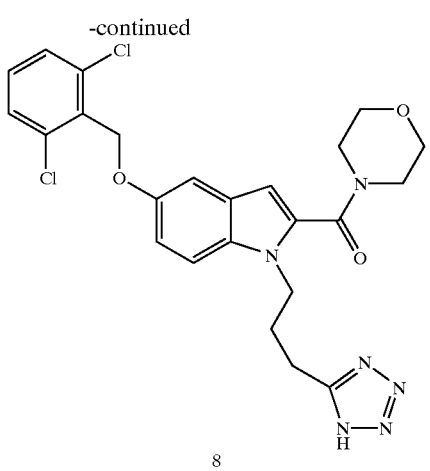

a) 1N NaOH, THF, MeOH; b) PyBrop, morpholine, Konig's base, DMAP, DMF; c) $Me_3Si-N_3$, $Bu_2Sn=O$, toluene, reflux Indole ethyl ester 4, Scheme 2, was saponified to the corresponding carboxylic acid 6 using aqueous NaOH, THF and MeOH. The acid was then converted to an amide using standard amide coupling reagents and the desired amine. In this example, the amine used was morpholine and the coupling reagent was PyBrop in the presence of Konig's base (diisopropylethylamine) and catalytic DMAP. This provided morpholino amide 7. Nitrile 7 was then converted to the tetrazole 8 according to the method outlined in Scheme 1.

Compounds of formula (I) wherein $R^1$ is an ethyl ester, $R^2$ is CHO, $R^3$ is 2,6-dichlorophenyl and n=3 were prepared by the method described in Scheme 3.

Scheme 3

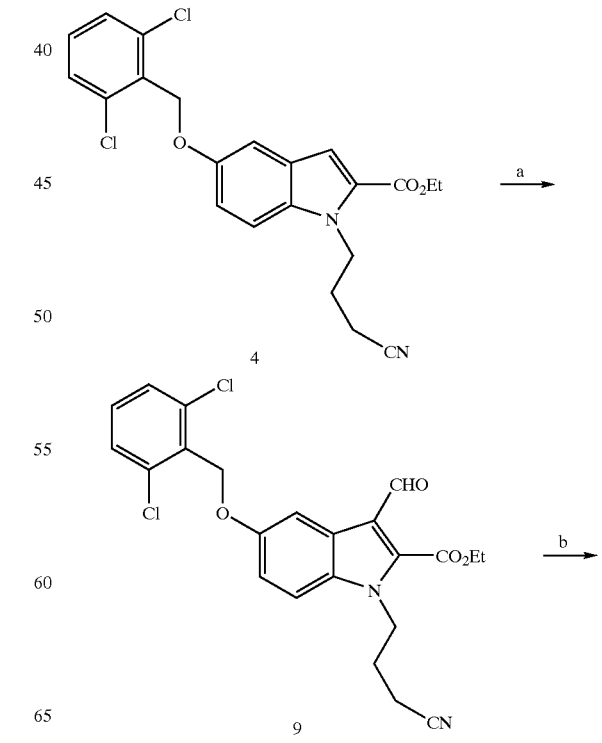

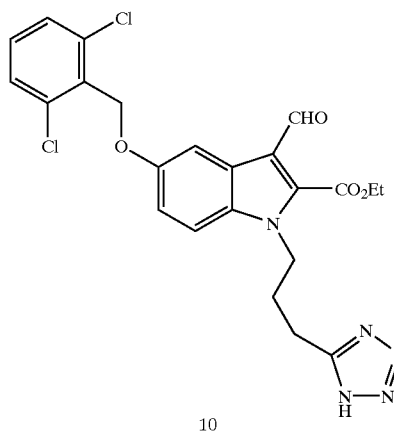

a) POCl$_3$, DMF; b) Me$_3$Si-N$_3$, Bu2Sn=O, toluene, reflux

Indole ethyl ester 4, Scheme 3, was converted to the C-3 aldehyde 9 using a Vilsmeier reaction (POCl$_3$, DMF). Nitrile 9 was then converted to the tetrazole 10 according to the method outlined in Scheme 1.

Compounds of formula (I) wherein R$^1$ is H, R$^2$ is H, R$^3$ is 2,6-dichlorophenyl and n=3 were prepared by the method described in Scheme 4.

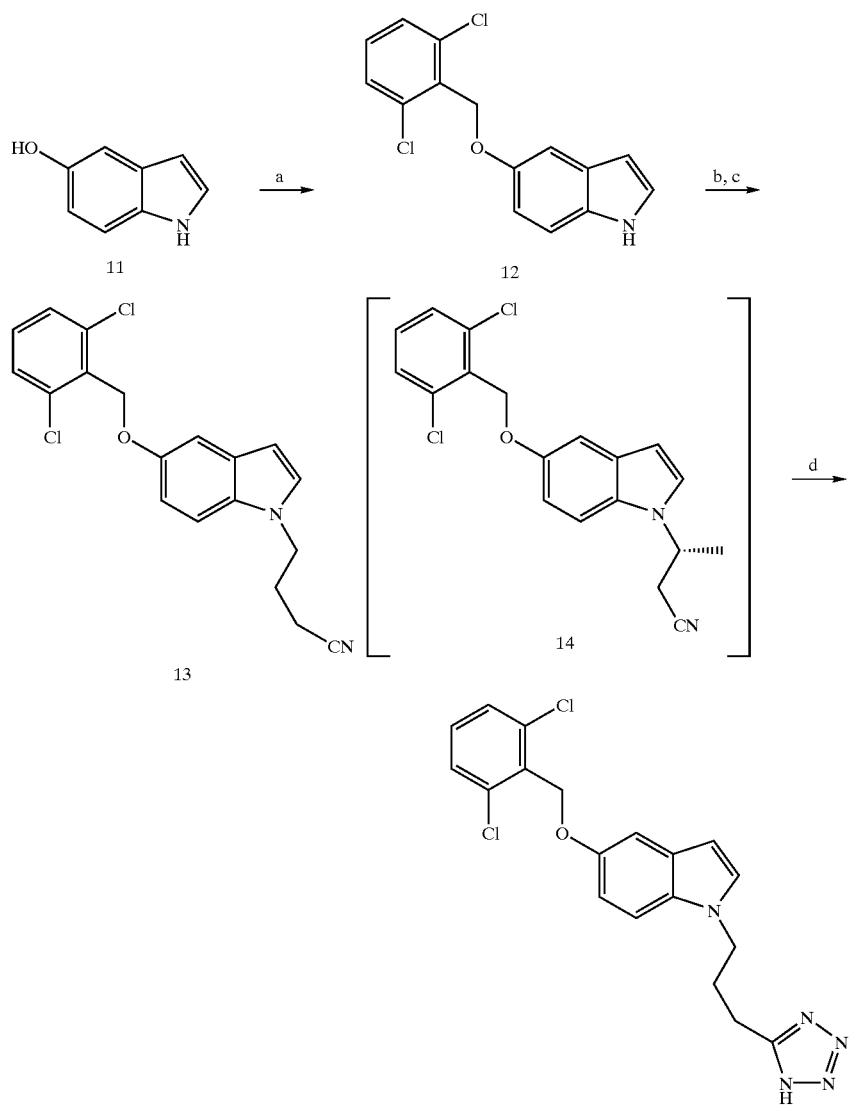

Scheme 4 a) 2,6-dichlorobenzyl bromide, Cs₂CO₃, DMF; b) NaH, 4-bromobutyronitrile, DMF; c) NaOMe, MeOH; d) Me₃Si-N₃, Bu₂Sn=O, toluene, reflux 5-Hydroxyindole (Aldrich), Scheme 4, was converted to the 2,6-dichlorobenzylether 12 according to methods outlined in Scheme 1. The indole nitrogen was then alkylated with 4-bromobutyronitrile as previously described (Scheme 1). However, in this instance, a mixture of products was obtained consisting of the desired nitrile 13 and the undesired product 14 in a ratio of 85:15. The undesired nitrile (14) was selectively decomposed by treating the mixture directly with sodium methoxide in MeOH providing 13 as the sole product. Nitrile 13 was then converted to the tetrazole 15 as previously outlined.

Compounds of formula (I) wherein $R^1$ is H, $R^2$ is ethyl ketone (—COEt), $R^3$ is 2,6-dichlorophenyl and n=3 were prepared by the method described in Scheme 5.

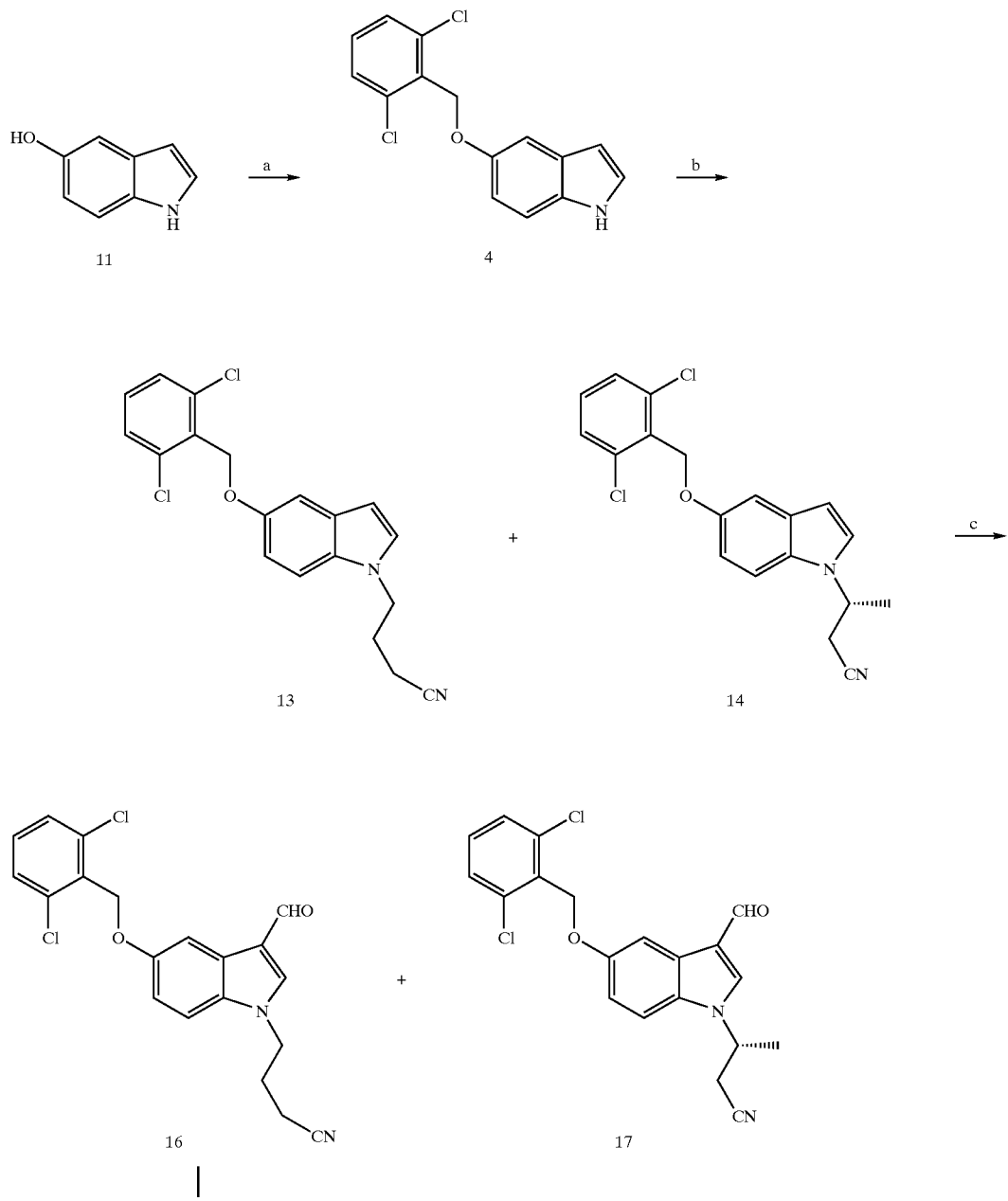

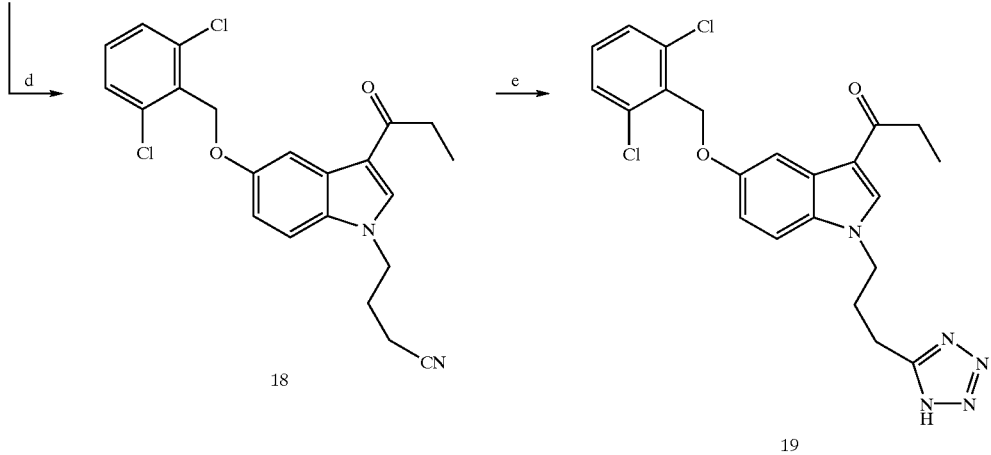

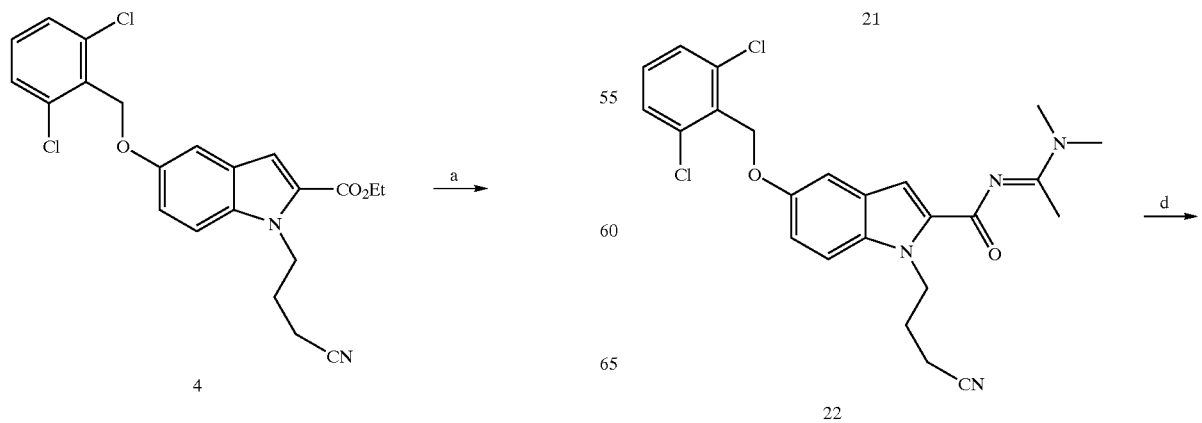

a) 2,6-dichlorobenzyl bromide, $Cs_2CO_3$, DMF; b) NaH, 4-bromobutyronitrile, DMF; c) i. $POCl_3$, DMF, ii. separate 16 from 17; d) EtMgBr, THF; e) $Me_3Si-N_3$, $Bu_2Sn=O$, toluene, reflux The mixture of nitriles, 13 and 14, were prepared as outlined in Scheme 4, however, in this instance the two compounds were not separated. The mixture was subjected to the Vilsmeier reaction ($POCl_3$, DMF) to provide the mixture of aldehydes, 16 and 17, which were readily separated using flash column chromatography. The pure aldehyde 16 was then reacted with the commercially available Grignard reagent ethyl magnesium bromide in an aprotic solvent such as THF or ether. Any desired Grignard or organo lithium reagent can be used at this stage. While the normal product from the Grignard reaction would be the secondary alcohol, in this example, the ketone 18 was isolated directly from the reaction mixture in low yield. The nitrile group of 18 was then converted to the desired tetrazole as previously described, thus providing 19.

Compounds of formula (I) wherein $R^1$ is a substituted oxadiazole, $R^2$ is H, $R^3$ is 2,6-dichlorophenyl and n=3 were prepared by the method described in Scheme 6.

Scheme 6

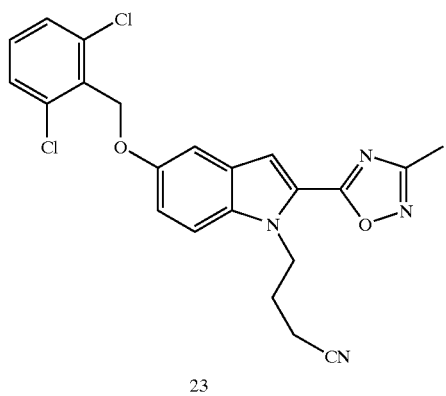

23

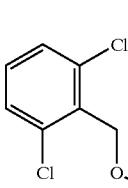

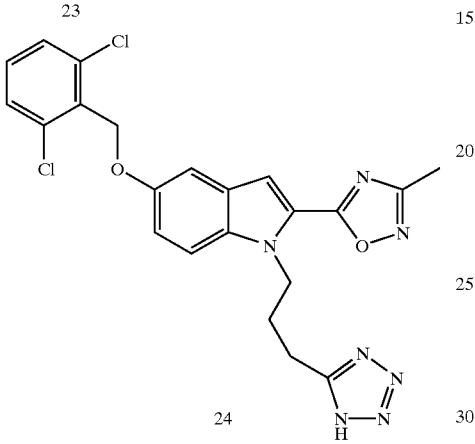

24 a) 1N NaOH, THF, EtOH; b) i. CDI, DMF, ii. NH$_3$, DMF; c) Me$_2$NCMe(OMe)$_2$, 110° C.; d) NH$_2$OH-HCl, AcOH, dioxane, 1N NaOH, 90° C.; e) Me$_3$Si-N$_3$, Bu$_2$Sn=O, toluene, reflux Nitrile—ester intermediate 4 was hydrolyzed to the corresponding carboxylic acid 20. Acid 20 was then activated using carbonyl diimidazole (CDI) followed by treatment with gaseous ammonia to form the primary amide 21. Reaction of 21 with dimethylacetamide dimethylacetal provided 22 which was then converted into the desired oxadiazole system via treatment with hydroxylamine, thus providing 23. The nitrile functional group of 23 was next converted to the tetrazole 24 by reaction with azide according to the previously described methods.

Compounds of formula (I) wherein R$^1$ is an oxazole, R$^2$ is H, R$^3$ is 2,6-dichlorophenyl and n=3 were prepared by the method described in Scheme 7.

Scheme 7

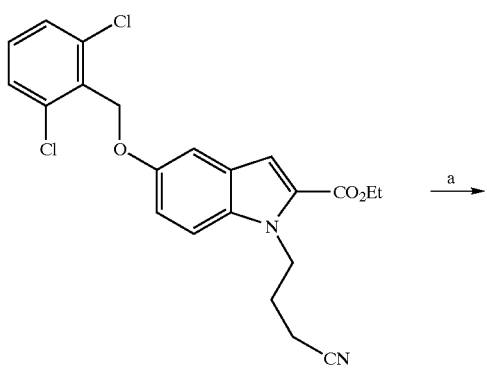

4

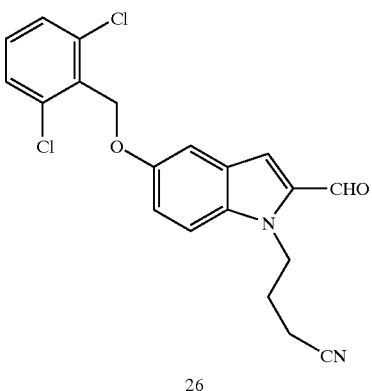

25

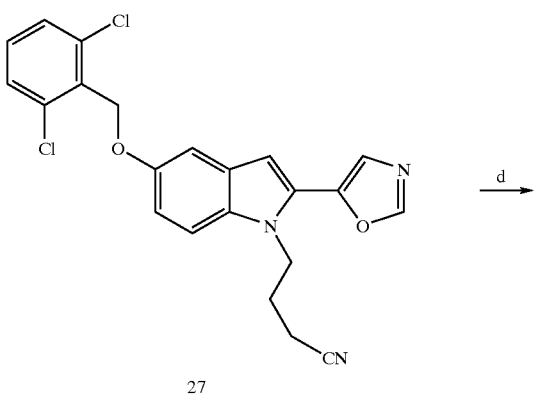

26

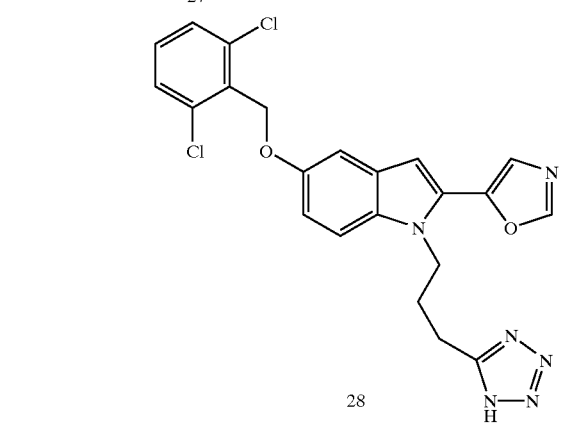

27

28 a) LiBH$_4$, THF; b) MnO$_2$, CH$_2$Cl$_2$; c) tol-SO$_2$CH$_2$NC, MeOH; d) Me$_3$Si-N$_3$, Bu$_2$Sn=O, toluene, reflux The ethyl ester of 4 was reduced to the corresponding primary alcohol 25 using lithium borohydride in THF. Oxidation with MnO$_2$ provided the aldehyde 26. Alternative oxidizing reagents such as Dess-Martin reagent, Swern oxidation or pyridine-SO$_3$ could also be used. Reaction of the aldehyde with tosylmethyl isocyanide yielded the oxazole 27 which was next converted to tetrazole 28 following standard methods.

Compounds of formula (I) wherein R$^1$ is an O-methyl oxime, R$^2$ is H, R$^3$ is 2,6-dichlorophenyl and n=3 were prepared by the method described in Scheme 8.

Scheme 8

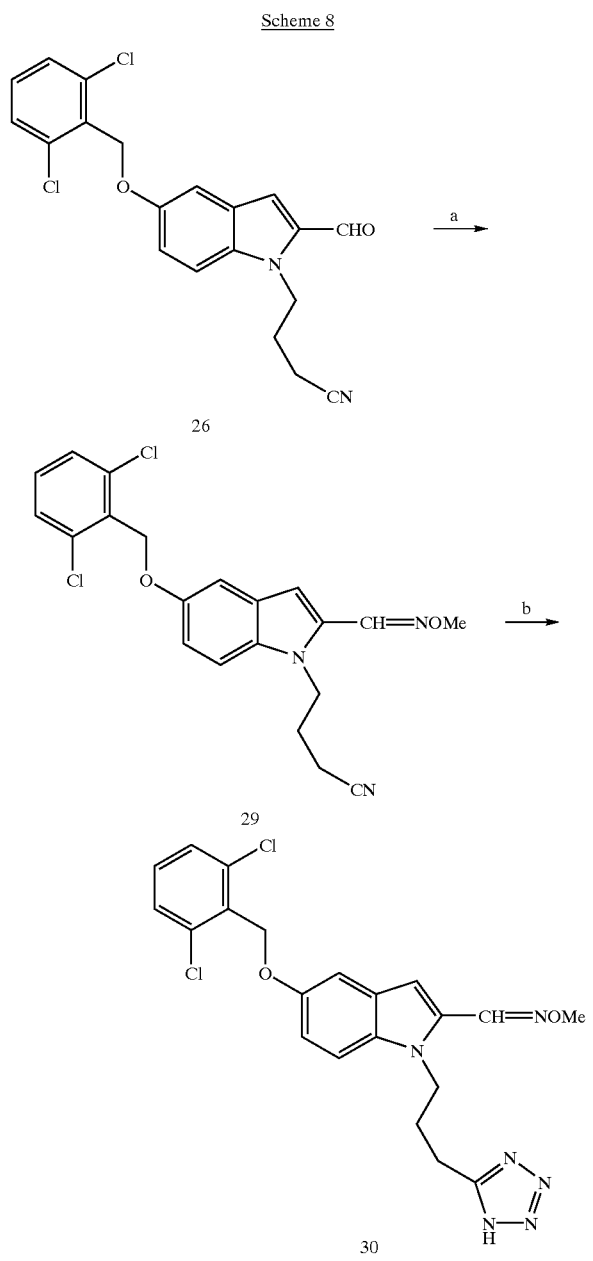

a) NH$_2$OMe.HCl, b) Me$_3$Si-N$_3$, Bu$_2$Sn=O, toluene, reflux

Aldehyde 26 was converted to the desired O-methyl oxime 29 via reaction with methoxyamine. The nitrile was then converted to the tetrazole 30 by reaction with azide as previously described.

Any of these compounds can potentially be used to treat any disease caused by pathogens that possess a type II fatty acid synthesis pathway, such as mycobacteria. Such diseases include, but are not limited to, malaria and tuberculosis.

SYNTHETIC EXAMPLES

The invention will now be described by reference to the following examples, which are merely illustrative and are not to be construed as a limitation of the scope of the present invention. All temperatures are given in degrees centigrade, and all solvents are highest available purity unless otherwise indicated.

Example 1

Preparation of 5-(2.6-Dichlorobenzyloxy)-1-[3-(1H-tetrazol-5-yl)propyl]-1H-indole-2-carboxylic Acid Ethyl Ester a) 5-Hydroxyindole-2-carboxylic Acid Ethyl Ester A solution of 5-benzyloxyindole-2-carboxylic acid ethyl ester (10 g, 34 mmol) in ethanol (250 mL) was treated with 10% Pd/C and hydrogenated under atmospheric pressure (double-walled balloon) for 20 h. The reaction mixture was diluted with EtOAc and filtered through Celite®. Evaporation of the filtrate in vacuo gave the title compound as a tan solid (7 g, 99%). $^1$H NMR (400 MHz, CDCl$_3$)·8.86 (br s, 1H), 7.29 (d, J=8.80 Hz, 1H), 7.11 (s, 1H), 7.06 (s, 1H), 6.94 (d, J=8.70 Hz, 1H), 4.83 (br s, 1H), 4.42 (q, J=7.09 Hz, 2H), 1.41 (t, J=7.08 Hz 3H).

b) 5-(2,6-Dichlorobenzyloxy)indole-2-carboxylic Acid Ethyl Ester

A solution of the compound of Example 1(a) (7 g, 34 mmol) in anhydrous DMF (100 mL) was treated with cesium carbonate (16.8 g, 52 mmol) and 2,6-dichlorobenzyl chloride (7.38 g, 38 mmol) and stirred at room temperature for 20 h. The reaction mixture was diluted with EtOAc and washed with water and brine. The organic extract was dried over Na$_2$SO$_4$, filtered, and concentrated in vacuo to give a crude solid. Trituration of the solid with methylene chloride provided 7.61 g (61%) of the title compound as an off-white solid. ES (MS) m/e 364.2 [M+H]$^+$.

c) 1-(3-Cyanopropyl)-5-(2,6-dichlorobenzyloxy)-1H-indole-2-carboxylic Acid Ethyl Ester To a solution of 5-(2,6-dichlorobenzyloxy)-1H-indole-2-carboxylic acid ethyl ester (1.50 g, 4.12 mmol) in dimethylformamide (15 mL) was added 60% sodium hydride (0.25 g, 6.18 mmol). The reaction mixture was stirred at ambient temperature under argon for 2.5 h. 4-Bromobutyronitrile (0.92 g, 6.14 mmol) was then added and the reaction mixture stirred for another 14 h at ambient temperature. The reaction was diluted with ethyl acetate and washed three times with water. The organic layer was dried over MgSO$_4$, filtered and the solvent removed under reduced pressure. Purification by flash chromatography (silica gel, 25% ethyl acetate/hexane) yielded an off-white solid (1.60 g, 95%). MS(ES) m/e 431.0 [M +H]$^+$.

d) 5-(2,6-Dichlorobenzyloxy)-1-[3-(1H-tetrazol-5-yl) propyl]-1H-indole-2-carboxylic Acid Ethyl Ester To a solution of 1-(3-cyanopropyl)-5-(2,6-dichlorobenzyloxy)-1H-indole-2-carboxylic acid ethyl ester (0.60 g, 1.39 mmol) in toluene (30 mL) was added azidotrimethylsilane (0.55 mL, 4.17 mmol) and dibutyltin oxide (0.10 g, 0.42 mmol). The reaction mixture was heated and stirred under argon at reflux temperature for 40 h. The solution was cooled and the toluene removed under reduced pressure. Methanol was then added and removed under reduced pressure. Ethyl acetate was added and the reaction mixture was washed with water and brine. The organic layer was dried over MgSO$_4$, filtered and the solvent removed under reduced pressure. Purification by flash chromatography (silica gel, 10% methanol/dichloromethane) yielded a white solid (0.58 g, 87%). MS(ES) m/e 474.2 [M +H]$^+$.

Example 2

Preparation of 1-{5-(2,6-dichlorobenzyloxy)-1-[3-(1H-tetrazol-5-yl)propyl]-1H-indol-2-yl}-1-morpholin-4-yl-methanone a) 1-(3-Cyanopropyl)-5-(2,6-dichlorobenzyloxy)-1H-indole-2-carboxylic Acid 1-(3-Cyanopropyl)-5-(2,6-dichlorobenzyloxy)-1H-indole-2-carboxylic acid ethyl ester (1.89 g, 4.38 mmol), from Example 1(c), was dissolved in tetrahydrofuran (5 mL). Methanol (5 mL) and 1.0 N NaOH (5 mL) were added and the reaction mixture was stirred at ambient temperature for 12 h. The tetrahydrofuran and methanol were removed under reduced pressure and water (10 mL) was added. The solution was acidified to pH 2 with 10% aqueous HCl solution. The product precipitated as a white solid (1.52 g, 86%) and was collected through vaccuum filtration. (MS (ES) m/e 403.0 [M +H]$^+$.

b) 4-[5-(2,6-Dichlorobenzyloxy)-2-(1-morpholin-4-yl-methanoyl)indol-1-yl]-butyronitrile 1-(3-Cyanopropyl)-5-(2,6-dichlorobenzyloxy)-1H-indole-2-carboxylic acid (0.10 g, 0.25 mmol) was dissolved in dimethylformamide (15 mL). PyBroP (bromo-tris-pyrrolidino-phosphonium hexafluorophosphate) (0.13 g, 0.27 mmol) was added followed by morpholine (0.065 g, 0.74 mmol), diisopropylethylamine (0.13 g, 0.99 mmol), and a catalytic amount of N,N-dimethylaminopyridine. The reaction mixture was stirred for 18 h under argon at ambient temperature. The solution was diluted with dichloromethane and washed with water (3×) and brine. The organic layer was dried over MgSO$_4$, filtered, and the solvent removed under reduced pressure. Purification by flash chromatography (silica gel, 25% acetone/chloroform) yielded an off-white solid (0.11 g, 95%). MS(ES) m/e 472.2 [M +H]$^+$.

c) 1-{5-(2,6-Dichlorobenzyloxy)-1-[3-(1H-tetrazol-5-yl)propyl]-1H-indol-2-yl}-1-morpholin-4-yl-methanone To a solution of 4-[5-(2,6-dichlorobenzyloxy)-2-(1-morpholin-4-yl-methanoyl)indol-1-yl]butyronitrile (0.085 g, 0.18 mmol) in toluene (10 mL) was added azidotrimethylsilane (0.071 mL, 0.54 mmol) and dibutyltin oxide (0.014 g, 0.054 mmol). The reaction mixture was heated to reflux and stirred under argon at reflux temperature for 40 h. The solution was then cooled and the toluene removed under reduced pressure. Methanol was then added and removed under reduced pressure. Ethyl acetate was added and the reaction mixture was washed with water and brine. The organic layer was dried over MgSO$_4$, filtered, and the solvent removed under reduced pressure. Purification by flash chromatography (silica gel, 10% methanol/dichloromethane) yielded a white solid (0.074 g, 79%). MS(ES) m/e 515.2 [M+H]$^+$.

Example 3

Preparation of 5-(2,6-Dichlorobenzyloxy)-1-[3-(1H-tetrazol-5-yl)propyl]-1H-indole-2carboxylic Acid Isobutyl Amide a) 1-(3-Cyanopropyl)-5-(2,6-Dichlorobenzyloxy)-1H-indole-2-carboxylic Acid Isobutyl Amide 1-(3-Cyanopropyl)-5-(2,6-dichlorobenzyloxy)-1H-indole-2-carboxylic acid (0.10 g, 0.25 mmol), from Example 2(a), was dissolved in dimethylformamide (15 mL). PyBroP (bromo-tris-pyrrolidino-phosphonium hexafluorophosphate) (0.13 g, 0.27 mmol) was added followed by isobutylamine (0.054 g, 0.74 mmol), diisopropylethylamine (0.13 g, 0.99 mmol), and a catalytic amount of N,N-dimethylaminopyridine. The reaction mixture was stirred for 18 h under argon at ambient temperature. The solution was diluted with dichloromethane and washed with water (3X) and brine. The organic layer was dried over MgSO$_4$, filtered, and the solvent removed under reduced pressure. Purification by flash chromatography (silica gel, 30% ethyl acetate/hexanes) yielded a white solid (0.076 g, 67%). MS(ES) m/e 458.2 [M +H]$^+$.

b) 5-(2,6-dichlorobenzyloxy)-1-[3-(1H-tetrazol-5-yl)propyl]-1H-indole-2-carboxylic Acid Isobutyl Amide To a solution of 1-(3-cyanopropyl)-5-(2,6-dichlorobenzyloxy)-1H-indole-2-carboxylic acid isobutyl amide (0.076 g, 0.17 mmol) in toluene (10 mL) was added azidotrimethylsilane (0.066 mL, 0.50 mmol) and dibutyltin oxide (0.012 g, 0.050 mmol). The reaction mixture was heated to reflux and stirred under argon at reflux temperature for 40 h. The solution was then cooled and the toluene removed under reduced pressure. Methanol was added and removed under reduced pressure. Ethyl acetate was added and the reaction mixture was washed with water and brine. The organic layer was dried over MgSO$_4$, filtered, and the solvent removed under reduced pressure. Purification by flash chromatography (silica gel, 10% methanol/dichloromethane) yielded a white solid (0.032 g, 38%). MS(ES) m/e 501.2 [M +H]$^+$.

Example 4

Preparation of 5-(2,6-Dichlorobenzyloxy)-1-[3-(1H-tetrazol-5-yl)propyl]-1H-indole-2-carboxylic Acid Diethylamide a) 1-(3-Cyanopropyl)-5-(2,6-dichlorobenzyloxy)-1H-indole-2-carboxylic Acid Diethylamide 1-(3-Cyanopropyl)-5-(2,6-dichlorobenzyloxy)-1H-indole-2-carboxylic acid (0.10 g, 0.25 mmol), from Example 2(a), was dissolved in dimethylformamide (15 mL). PyBroP (bromo-tris-pyrrolidino-phosphonium hexafluorophosphate) (0.13 g, 0.27 mmol) was added followed by diethylamine (0.054 g, 0.74 mmol), diisopropylethylamine (0.13 g, 0.99 mmol), and a catalytic amount of N,N-dimethylaminopyridine. The reaction mixture was stirred for 18 h under argon at ambient temperature. The solution was diluted with dichloromethane and washed with water (3X) and brine. The organic layer was dried over MgSO$_4$, filtered, and the solvent removed under reduced pressure. Purification by flash chromatography (silica gel, 30% ethyl acetate/hexanes) yielded a white solid (0.078 g, 69%). MS(ES) m/e 458.2 [M +H]$^+$.

b) 5-(2,6-Dichlorobenzyloxy)-1-[3-(1H-tetrazol-5-yl)propyl]-1H-indole-2-carboxylic Acid Diethylamide To a solution of 1-(3-cyanopropyl)-5-(2,6-dichlorobenzyloxy)-1H-indole-2-carboxylic acid diethylamide (0.078 g, 0.17 mmol) in toluene (10 mL) was added azidotrimethylsilane (0.066 mL, 0.50 mmol) and dibutyltin oxide (0.012 g, 0.050 mmol). The reaction mixture was heated to reflux and stirred under argon at reflux temperature for 40 h. The solution was cooled and the toluene removed under reduced pressure. Methanol was then added and removed under reduced pressure. Ethyl acetate was added and the reaction mixture was washed with water and brine. The organic layer was dried over MgSO$_4$, filtered, and the solvent removed under reduced pressure. Purification by flash chromatography (silica gel, 10% methanol/dichloromethane) yielded a white solid (0.040 g, 47%). MS(ES) m/e 501.2 [M +H]$^+$.

Example 5

Preparation of 5-(2,6-Dichlorobenzyloxy)-3-formyl-1-[3-(1H-tetrazol-5-yl)propyl]-1H-indole-2-carboxylic Acid Ethyl Ester.

a) 1-(3-Cyanopropyl)-5-(2,6-dichlorobenzyloxy)-3-formyl-1H-indole-2-carboxylic Acid Ethyl Ester.

To phosphorous oxychloride (0.13 mL, 1.39 mmol) at 0° C. was added via dropwise addition DMF (0.43 mL, 3.58 mmol) followed by 1-(3-cyanopropyl)-5-(2,6-dichlorobenzyloxy)-1H-indole-2-carboxylic acid ethyl ester (0.5 g, 1.16 mmol), from Example 1(c), in DMF (1 mL). The resulting mixture was stirred at room temperature for 30 min followed by heating at 50° C. for 4 h. The mixture was poured into ice water and neutralized by the addition of 1N sodium hydroxide. The precipitated solid was filtered, washed with water and dried in vacuo to give the desired product as a solid (0.5 g, 94%). LS/MS (ES+) m/e 459 [M+H]$^+$.

b) 5-(2,6-Dichlorobenzyloxy)-3-formyl-1-[3-(1H-tetrazol-5-yl)propyl]-1H-indole-2-carboxylic Acid Ethyl Ester.

Following the procedure of Example 1(d), the title compound was obtained as a brown solid (0.021 g, 55%). LS/MS (ES+) m/e 502 [M+H]$^+$.

Example 6

Preparation of 5-(2,6-dichlorobenzyloxy)-2-(3-methyl-[1,2,4]oxadiazol-5-yl)-1-[3-(1H-tetrazol-5-yl)propyl]-1H-indole.

a) 1-(3-Cyanopropyl)-5-(2,6-Dichlorobenzyloxy)-1H-indole-2-carboxylic Acid.

To a solution of 1-(3-cyanopropyl)-5-(2,6-dichlorobenzyloxy)-1H-indole-2-carboxylic acid ethyl ester (0.6 g, 1.4 mmol), from Example 1(c), in THF (5 mL) and EtOH (5 mL) was added 1N NaOH (1 mL). The reaction mixture was stirred at room temperature for 24 h. The resulting mixture was concentrated in vacuo and diluted with H$_2$O and acidified to pH 5 with 1N HCl. The precipitated solid was filtered and washed with H$_2$O and dired in vacuo to give a solid (0.5 g, 95%). LC/MS (ES+) m/e 403[M+H]$^+$.

b) 1-(3-Cyanopropyl)-5-(2,6-Dichlorobenzyloxy)-1H-indole-2-carboxylic Acid Amide.

To a solution of 1-(3-cyanopropyl)-5-(2,6-dichlorobenzyloxy)-1H-indole-2-carboxylic acid (0.5 g, 1.2 mmol) in DMF (3 mL) was added carbonyl diimidazole (CDI; 0.26 g, 1.6 mmol). The resulting mixture was stirred at room temperature for 24 h. Ammonia gas was gently bubbled into the reaction solution for 1 h. The reaction solution was stirred at room temperature for an additional 12 h. The reaction mixture was poured into water and extracted with EtOAc (2X). The combined organic layers were washed with H$_2$O, brine, dried (NaSO4), filtered, and concentrated in vacuo to give a solid (0.38 g, 80%). LC/MS (ES+) m/e 402[M+H]$^+$.

c) 1-(3-Cyanopropyl);-5-(2,6-dichlorobenzyloxy)-1H-indole-2-carboxylic acid (1-dimethylaminoethylidene)amide.

To 1-(3-cyanopropyl)-5-(2,6-dichlorobenzyloxy)-1H-indole-2-carboxylic acid amide (0.38 g, 0.94 mmol) was added dimethylacetamide dimethylacetal (0.45 g). The resulting mixture was heated at 110° C. for 1 h. The reaction mixture was concentrated in vacuo to give a brown gum (0.5 g, 85%) which was used in the next step without further manipulation.

d) 5-(2,6-Dichlorobenzyloxy)-2-(3-methyl-[1,2,4]oxadiazol-5-yl-indol-1-yl)butyronitrile To a solution of 1-(3-cyanopropyl)-5-(2,6-dichlorobenzyloxy)-1H-indole-2-carboxylic acid (1-dimethylaminoethylidene)amide (0.36 g, 0.6 mmol) in dioxane (1mL) was added hydroxylamine hydrochloride (0.070 g, 0.9 mmol) followed by acetic acid (1 mL) and 1N NaOH (1 mL). The resulting mixture was heated at 90° C. for 2 h. The reaction mixture was cooled and diluted with H$_2$O. The precipitated solid was washed with H$_2$O and dried under vacuum to give the desired material as a solid (0.25 g, 75%). LC/MS (ES+) m/e 441 [M+H]$^+$.

e) 5-(2,6-Dichlorobenzyloxy)-2-(3-methyl-[-1,2,4]oxadiazol-5-yl)-1-[3-(1H-tettrazol-5-yl)propyl]-1H-indole.

Following the procedure of Example 1(d), the title compound was obtained as a solid (0.10 g, 57%). LS/MS (ES+) m/e 484 [M+H]$^+$.

Example 7

Preparation of 5-(2,6-dichlorobenzyloxy)-1-[3-(1H-tetrazol-5-yl)propyl]-1H-indole a) 5-(2,6-Dichlorobenzyloxy)-1H-indole To a solution of 5-hydroxyindole (5.0 g, 37.6 mmol) in dimethylformamide (200 mL) at room temperature was added cesium carbonate (18.4 g, 56.3 mmol). The reaction mixture was stirred at 60° C. for 30 min followed by the addition of 2,6-dichlorobenzyl bromide (9.0 g, 37.6 mmol). After stirring at 60° C. for 16 h, the reaction solution was partitioned between ethyl acetate and water. The organic layer was washed with brine and dried (Na$_2$SO$_4$). Purification by flash column chromatography (silica gel, hexane/ethyl acetate) yielded a clear oil (8.05 g, 73%). MS(ES) m/e 292.0 [M+H]$^+$.

b) 4-[5-(2,6-Dichlorobenzyloxy)indol-1-yl]butyronitrile

To a solution of 5-(2,6-dichlorobenzyloxy)-1H-indole (2.0 g, 6.85 mmol) in dimethylformamide (30 mL) at ambient temperature was added sodium hydride (0.41 g, 10.3 mmol, 60% in mineral oil). After stirring at ambient temperature for 1 h, 4-bromobutyronitrile (1.01 g, 0.68 mL, 6.85 mmol) was added followed by the addition of tetrabutylammonium iodide (0.25 g, 0.68 mmol). After stirring at room temperature for 24 h, the reaction mixture was partitioned between ethyl acetate and water. The organic layer was washed with brine and dried (Na$_2$SO$_4$). Purification by flash column chromatography (silica gel, hexanes/ethyl acetate) yielded a mixture (1.37 g total weight) of desired product (85%) and undesired product 3-[5-(2,6-dichlorobenzyloxy)indole-1-yl]butyronitrile (15%). The two component mixture (0.12 g total weight) was treated with sodium methoxide (catalytic) in methanol/THF at room temperature for 16 h. The undesired product was decomposed and purification by flash column chromatography (silica gel, hexanes/ethyl acetate) afforded the desired product as a clear oil (0.1 g). MS(ES) m/e 359.0 [M+H]$^+$.

c) 5-(2,6-Dichlorobenzyloxy)-1-[3-(1H-tetrazol-5-yl)propyl]-1H-indole

To a solution of 4-[5-(2,6-dichlorobenzyloxy)indole-1-yl] butyronitrile (0.1 g, 0.28 mmol) in toluene (3 mL) was added azidotrimethylsilane (0.11 mL, 0.83 mmol) and dibutyltin oxide (0.021 g, 0.083 mmol). The reaction was refluxed for 16 h. The solvent was removed under reduced pressure and the crude product was purified by flash column chromatography (silica gel, dichloromethane/methanol) to yield a white foaming solid (0.067 g, 59%). MS(ES) m/e 402.0 [M+H]$^+$.

Example 8

Preparation of 1-{5-(2,6-dichlorobenzyloxy)-1-[3-(1H-tetrazol-5-yl)propyl]-1H-indol-3-yl}-pronan-1-one a) 4-[5-(2,6-Dichlorobenzyloxy)-3-formyl-indol-1-yl]butyronitrile A flame dried flask under argon was charged with DMF (0.43 mL, 5.57 mmol) and cooled to 0° C. Phosphorus oxychloride (0.16 mL, 1.67 mmol) was slowly added to the cooled DMF. The solution was stirred at 0° C. for 1 min and to this was added a DMF (1.5 mL) solution of a mixture of 4-[5-(2,6-dichlorobenzyloxy)indol-1-yl]butyronitrile (85%) and 3-[5-(2,6-dichlorobenzyloxy)indol-1-yl]butyronitrile (15%) (0.5 g, 1.4 mmol). The reaction mixture was stirred at room temprature for 1 h and heated at 50° C. for 4 h. The reaction solution was poured into ice water. A light yellow colored sticky solid precipated immediately. The mixture was neutralized by adding 1N NaOH until a pH of 7 was obtained. The product was extracted into ethyl acetate (3×) and the combined organic layers were washed with brine and dried over $Na_2SO_4$. The solvent was removed under reduced pressure and the resulting crude yellow oil was purified by flash column chromatography (silica gel, ethyl acetate/hexane) to yield the desired aldehyde as a white solid (0.38 g, 70%) and the undesired aldehyde (0.099 g, 18%).MS(ES) m/e 387.0 [M+H]$^+$.

b) 4-[5-(2,6-Dichlorobenzyloxy)-3-propionyl-indol-1-yl]butyronitrile

To a flame dried flask was added a solution of 4-[5-(2,6-dichlorobenzyloxy)-3-formyl-indol-1-yl]butyronitrile (0.23 g, 0.59 mmol) in THF (10 mL) and cooled to −78° C. To this solution ethyl magnesium bromide (1.0M in THF, 0.65 mL, 0.65 mmol) was added via dropwise addition. The reaction was stirred at −78° C. for 3 h then warmed to room temperature slowly. After stirring at room temperature for 18 h, the reaction was partitioned between ethyl acetate and water. The organic layer was washed with brine and dried over $Na_2SO_4$. Purification by flash column chromatography (silica gel, ethyl acetate/hexane) afforded three products, one of which was identified by NMR, IR and LC-MS as the ketone 4-[5-( 2,6-dichlorobenzyloxy)-3-propionyl-indol-1-yl]butyronitrile (0.034 g, 14%). MS(ES) m/e 415.0 [M+H]$^+$. None of the expected secondary alcohol was recovered.

c) 1-{5-(2,6-Dichlorobenzyloxy)-1-[3-(1H-tetrazol-5-yl)propyl]-1H-indol-3-yl}propan-1-one To a solution of 4-[5-(2,6-dichlorobenzyloxy)-3-propionyl-indol-1-yl]butyronitrile (0.034 g, 0.08 mmol) in toluene (3 mL) was added azidotrimethylsilane (0.033 mL, 0.25 mmol) and dibutyltin oxide (0.006 g, 0.02 mmol). The reaction was refluxed for 16 h. The solvent was removed under reduced pressure and the crude product was purified by HPLC to yield a white solid (0.017 g, 46%). MS(ES) m/e 458.0 [M+H]$^+$.

Example 9

Preparation of 5-(2,6-dichlorobenzyloxy)-1-[3-(1H-tetrazol-5-yl)propyl]-1H-indole-2-carbaldehyde-O-methyl Oxime a) 4-[5-(2,6-Dichlorobenzyloxy)-2-hydroxymethyl-indol-1-yl]butyronitrile To a solution of 1-(3-cyanopropyl)-5-(2,6-dichlorobenzyloxy)-1H-indole-2-carboxylic acid ethyl ester (2.0 g, 4.64 mmol), from Example 1(c), in THF (20 mL) at room temperature was added lithium borohydride (0.25g, 11.6 mmol). The reaction was refluxed for 20 h and then quenched slowly by adding methanol until the evolution of gas ceased. The reaction was partitioned between ethyl acetate and water. The organic layer was washed with brine and dried over $Na_2SO_4$. Filtration and evaporation of the solvent yielded the desired alcohol as a white solid (1.73 g, 96%). MS(ES) m/e 389.0 [M+H]$^+$.

b) 4-[5-(2,6-Dichlorobenzyloxy)-2-formyl-indol-1-yl]butyronitrile

To a solution of 4-[5-(2,6-dichlorobenzyloxy)-2-hydroxymethyl-indol-1-yl]butyronitrile (1.73 g, 4.44 mmol) in $CH_2Cl_2$ (100 mL) was added $MnO_2$ (3.09 g, 35.6 mmol) and the reaction was stirred at room temperature for 18 h. The reaction mixture was filtered through Celite and the filtrate was concentrated under reduced pressure. Purification by flash column chromatography (silica gel, ethyl acetate/hexane) yielded the desired aldehyde (1.25 g, 73%) as a white solid. MS(ES) m/e 387.0 [M+H]$^+$.

c) 4-[5-(2,6-Dichlorobenzyloxy)-2-(methoxyiminomethyl)indol-1-yl]butyronitrile

To a solution of 4-[5-(2,6-dichlorobenzyloxy)-2-formyl-indol-1-yl]butyronitrile (0.1 g, 0.26 mmol) in pyridine (5 mL) was added methoxyamine hydrochloride (0.032 g, 0.39 mmol). After stirring at room temperature for 18 h, the solvent was removed under reduced pressure. The resulting crude product was purified by flash column chromatography (silica gel, ethyl acetate/hexane) to yield the desired O-methyl oxime (0.077 g, 71%) as a white solid. MS(ES) m/e 416.0 [M+H]$^+$.

d) 5-(2,6-Dichlorobenzyloxy)-1-[3-(1H-tetrazol-5-yl)propyl]-1H-indole-2-carbaldehyde-O-methyl Oxime To a solution of 4-[5-(2,6-dichlorobenzyloxy)-2-(methoxyiminomethyl)indol-1-yl]butyronitrile (0.07 g, 0.17 mmol) in toluene (3 mL) was added azidotrimethylsilane (0.067 mL, 0.55 mmol) and dibutyltin oxide (0.014 g, 0.055 mmol). The reaction was refluxed for 16 h. The solvent was removed under reduced pressure and the crude product was purified by HPLC to yield a yellow foaming solid (0.045 g, 58%). MS(ES) m/e 459.0 [M+H]$^+$.

Example 10

Preparation of 5-(2,6-dichlorobenzyloxy)-2-(oxazol-5-yl)-1-[3-(1H-tetrazol-5-yl)propyl]-1H-indole a) 4-[5-(2,6-dichlorobenzyloxy)-2-(oxazol-5-yl)indol-1-yl]butyronitrile A mixture of 4-[5-(2,6-dichlorobenzyloxy)-2-formyl-indol-1-yl]butyronitrile (0.2 g, 0.52 mmol), from Example 9(b), $K_2CO_3$ (0.14 g, 1.03 mmol) and tosylmethyl isocyanide (0.11 g, 0.57 mmol) in MeOH (15 mL) was stirred at room temperature for 5 min followed by reflux for 3 h to give a clear yellow solution. The solvent was removed under reduced pressure and the resulting solid was partitioned between chloroform and water. The aqueous layer was washed with chloroform twice and the combined organic layers were washed with water, brine and dried over $Na_2SO_4$. After filtration, the yellow filtrate was concentrated to yield the desired oxazol (0.21 g, 95%) as a yellow oil. MS(ES) m/e 426.0 [M+H]$^+$.

b) 5-(2,6-Dichlorobenzyloxy)-2-(oxazol-5-yl)-1-[3-(1H-tetrazol-5-yl)propyl]-1H-indole To a solution of 4-[5-(2,6-dichlorobenzyloxy)-2-(oxazol-5-yl)indol-1-yl]butyronitrile (0.21 g, 0.49 mmol) in toluene (10 mL) was added azidotrimethylsilane (0.20 mL, 1.48 mmol) and dibutyltin oxide (0.037 g, 0.148 mmol). The reaction was refluxed for 16 h. The solvent was removed under reduced pressure and the crude product was purified by flash column chromatography (silica gel, MeOH/$CH_2Cl_2$) to yield a yellow solid (0.18 g, 78%). MS(ES) m/e 469.0 [M+H]$^+$.

Biological Assay:

FabH was assayed in a coupled format using his-tagged S.aureus FabD, and acyl carrier protein (ACP) purchased from Sigma. Lyophilized ACP was reduced using β-mercaptoethanol in phosphate buffer. Malonyl-CoA, and FabD were added to the reduced ACP, thus generating malonyl-ACP. After the FabD reaction reached equilibrium, [$^{14}$C] acetyl-CoA and inhibitors were added, and the reaction started by the addition of FabH. TCA precipitation and filtration was used to separate [$^{14}$C] acetyl-CoA substrate from [$^{14}$C] acetoacetyl-ACP product.

Secondary and tertiary screens of suitable reproducibility, sensitivity, throughput and analytical power to progress primary screen hits are characterized, validated and in current use. Compounds are evaluated against purified mammalian fatty acid biosynthetic enzymes, E. coli FabH, FabB and a human lung cell cytotoxicity assay.

In addition, whole-cell antibacterial activity is determined against a range of clinically relevant wild type and efflux impaired bacteria using standard and novel fluorescence based technologies. The FabH assay has been thoroughly characterized kinetically and a reaction mechanism proposed. Detailed studies have generated novel data about mechanism of inhibition by tool compounds, including thiolactomycin. Screens in use are of direct relevance to the therapeutic goal—eradication of bacteria from sites of infection ('cure'). Several state-of-the-art animal models of bacterial infection are available, meaningful and in current use in this and numerous other studies at SB. Extensive prior experience with known antibacterials confirm that bacterial kill in vitro and in animal models is an excellent indicator of bacterial kill in vivo and cure of infection.

The present invention also provides a pharmaceutical composition, which comprises a compound of formula (I) or a pharmaceutically acceptable salt or in vivo hydrolysable ester thereof, and a pharmaceutically acceptable carrier. The compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral, especially oral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the compound of Formula (I) Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 1 to 140 mg/g of body weight, depending on the route and frequency of administration. Inhibitors of β-ketoacyl-ACP Synthase (FabH) can be administered by injection in solutions either intravenously, intramuscularly, intraperitoneally, or orally. The solution preferably contains a buffer (such as phosphate) to keep the pH in the range of about 3.5 to 7. DMSO or alcoholic solvents may also be present (at concentrations such as 0.01 to 10 mL/liter) to aid solubility and penetration of the β-ketoacyl-ACP Synthase (FabH) inhibitor.

No unacceptable toxicological effects are expected when a compound of formula (Ia) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or compounds which enhance the antibacterial activity of a compound of formula (I) may be employed.

The antibiotic compounds of the present invention are active against a wide range of organisms including both Gram-negative organisms such as *Eschierichia coli* and Klebsiella pneumoniae and Gram-positive organisms such as *Staphylococcus aureus, Streptococcus pneumoniae, Enterococcus faecalis and Enterococcus faecium*, including isolates resistant to existing antibiotics.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

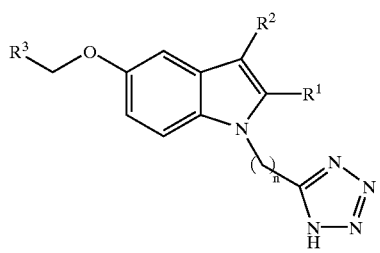

(I)

wherein,

R$^1$ is selected from the group consisting of H, CO$_2$R$^4$, COR$^4$, CONR$^5$R$^6$, CH(OH)R$^4$, CR$^4$=NOR4, heteroaryl and substituted heteroaryl;

R$^2$ is selected from the group consisting of H, COR$^4$, and CH(OH)R$^4$;

R$^3$ is selected from the group consisting of aryl, substituted aryl, heteroaryl and substituted heteroaryl;

R$^4$ is H or lower alkyl;

R$^5$ and R$^6$ are, independently, H, or lower alkyl or, together, form a 5 or 6 membered ring selected from the group consisting of piperidine, piperazine, pyrrolidine, morpholine and hydroxy piperidine; and n is an integer from 1 to 6;

or a pharmaceutically acceptable salt thereof or a pharmaceutically acceptable salt complex thereof.

2. A compound according to claim 1 selected from the group consisting of:

5-(2,6-dichlorobenzyloxy)-1-[3-(1H-tetrazol-5-yl)propyl]1H-indole-2-carboxylic acid ethyl ester;

1-{5-(2,6-dichlorobenzyloxy)-1-[3-(1H-tetrazol-5-yl)propyl]-1H-indol-2-yl}-1-morpholin-4-yl-methanone;

5-(2,6-dichlorobenzyloxy)-1-[3-(1H-tetrazol-5-yl)propyl]-1H-indole-2-carboxylic acid isobutyl amide;

5-(2,6-dichlorobenzyloxy)-1-[3-(1H-tetrazol-5-yl)propyl]-1H-indole-2-carboxylic acid diethylamide;

5-(2,6-dichlorobenzyloxy)-3-formyl-1-[3-(1H-tetrazol-5-yl)propyl]-1H-indole-2-carboxylic acid ethyl ester;

5-(2,6-dichlorobenzyloxy)-2-(3-methyl-[1,2,4]oxadiazol-5-yl)-1-[3-(1H-tetrazol-5-yl)propyl]-1H-indole;

5-(2,6-dichlorobenzyloxy)-1-[3-(1H-tetrazol-5-yl)propyl]-1H-indole;

1-{5-(2,6-dichlorobenzyloxy)-1-[3-(1H-tetrazol-5-yl)-propyl]-1H-indol-3-yl}propan-1-one;

5-(2,6-dichlorobenzyloxy)-1-[3-(1H-tetrazol-5-yl)propyl]-1H-indole-2-carbaldehyde-O-methyl oxime; and 5-(2,6-dichlorobenzyloxy)-2-(oxazol-5-yl)-1-[3-(1H-tetrazol-5-yl)propyl]-1H-indole.

3. A method of treating bacterial infections by administering to a patient in need thereof an effective amount of a compound of Formula (I) according to claim 1.

4. A method of treatment according to claim 1 wherein the compound of Formula (I) is selected from the group consisting of:

5-(2,6-dichlorobenzyloxy)-1-[3-(1H-tetrazol-5-yl)propyl]-1H-indole-2-carboxylic acid ethyl ester;

1-{5-(2,6-dichlorobenzyloxy)-1-[3-(1H-tetrazol-5-yl)propyl]-1H-indol-2-yl}-1-morpholin-4-yl-methanone;

5-(2,6-dichlorobenzyloxy)-1-[3-(1H-tetrazol-5-yl)propyl]-1H-indole-2-carboxylic acid isobutyl amide;

5-(2,6-dichlorobenzyloxy)-1-[3-(1H-tetrazol-5-yl)propyl]-1H-indole-2-carboxylic acid diethylamide;

5-(2,6-dichlorobenzyloxy)-3-formyl-1-[3-(1H-tetrazol-5-yl)propyl]-1H-indole-2-carboxylic acid ethyl ester;

5-(2,6-dichlorobenzyloxy)-2-(3-methyl-[1,2,4]oxadiazol-5-yl)-1-[3-(1H-tetrazol-5-yl)propyl]-1H-indole;

5-(2,6-dichlorobenzyloxy)-1-[3-(1H-tetrazol-5-yl)propyl]-1H-indole;

1-{(5-(2,6-dichlorobenzyloxy)-1-[3-(1H-tetrazol-5-yl)-propyl]-1H-indol-3-yl}propan-1-one;

5-(2,6-dichlorobenzyloxy)-1-[3-(1H-tetrazol-5-yl)propyl]-1H-indole-2-carbaldehyde-O-methyl oxime; and 5-(2,6-dichlorobenzyloxy)-2-(oxazol-5-yl)-1-[3-(1H-tetrazol-5-yl)propyl]-1H-indole.

* * * * *